US012377148B2

(12) United States Patent
Sczakiel et al.

(10) Patent No.: US 12,377,148 B2
(45) Date of Patent: Aug. 5, 2025

(54) COMPOSITION FOR ADMINISTERING AND RELEASING OLIGONUCLEOTIDES

(71) Applicant: Paricam Therapeutics GmbH, Berlin (DE)

(72) Inventors: Georg Alois Sczakiel, Groß-Grönau (DE); Thomas Manfred Rupp, Berlin (DE); Wolfgang Nedbal, Aglasterhausen-Breitenbronn (DE)

( * ) Notice: Subject to any disclaimer, the term of this patent is extended or adjusted under 35 U.S.C. 154(b) by 1026 days.

(21) Appl. No.: 17/425,853

(22) PCT Filed: Jan. 15, 2020

(86) PCT No.: PCT/EP2020/050866
§ 371 (c)(1),
(2) Date: Jul. 26, 2021

(87) PCT Pub. No.: WO2020/151999
PCT Pub. Date: Jul. 30, 2020

(65) Prior Publication Data
US 2022/0160873 A1 May 26, 2022

(30) Foreign Application Priority Data
Jan. 25, 2019 (EP) ..................... 19153663

(51) Int. Cl.
*A61K 47/10* (2017.01)
*A61K 9/00* (2006.01)
*A61K 31/7088* (2006.01)
*A61K 47/18* (2017.01)

(52) U.S. Cl.
CPC .............. *A61K 47/10* (2013.01); *A61K 9/006* (2013.01); *A61K 9/0063* (2013.01); *A61K 31/7088* (2013.01); *A61K 47/183* (2013.01)

(58) Field of Classification Search
CPC .. A61K 47/10; A61K 31/7088; A61K 47/183; A61K 9/0063; A61K 9/006
See application file for complete search history.

(56) References Cited

U.S. PATENT DOCUMENTS

| 11,008,574 | B2 * | 5/2021 | Sczakiel .................. A61P 1/02 |
| 2007/0135364 | A1 | 6/2007 | Bennett et al. |
| 2013/0079388 | A1 | 3/2013 | Becker et al. |
| 2017/0014514 | A1 | 1/2017 | Simmons et al. |

FOREIGN PATENT DOCUMENTS

| EP | 1115858 B1 | 4/2003 | |
| JP | 2002535377 A | 10/2002 | |
| WO | WO-2004016224 A2 * | 2/2004 | ......... C12N 15/1136 |

OTHER PUBLICATIONS

Bodratti et al., "Formulation of Poloxamers for Drug Delivery", Journal of Functional Biomaterials, Published Jan. 18, 2018, pp. 1-24. (Year: 2018).*
Wan et al., "The Medicinal Chemistry of Therapeutic Oligonucleotides", The Journal of Medicinal Chemistry, Published Jul. 19, 2016, pp. 9645-9658. (Year: 2016).*
Nedbal et al., "Antisense-Mediated Inhibition of ICAM-1 Expression: A Therapeutic Strategy Against Inflammation of Human Periodontal Tissue", Antisense and Nucleic Acid Drug Development, Published 2002, pp. 71-78. (Year: 2002).*
Akkari et al., "Poloxamer 407/188 binary thermosensitive hydrogels as delivery systems for infiltrative local anesthesia: Physicochemical characterization and pharmacological evaluation", Materials Science and Engineering C, Published May 20, 2016, pp. 299-307. (Year: 2016).*
English Translation of Claims for WO 200018907, Published Apr. 6, 2000, pp. 1-2. (Year: 2000).*
English Translation of Description for WO 200018907, Published Apr. 6, 2000, pp. 1-13. (Year: 2000).*
Dumortier, G , et al., "A review of poloxamer 407 pharmaceutical and pharmacological characteristics", Pharmaceutical Research 23(12), 2709-2728 (2006).
Kretschmer-Kazemi Far, R , et al., "Technical Improvements in the Computational Target Search for Antisense Oligonucleotides", Oligonucleotides 15, 223-233 (2005).
Nedbal, W , et al., "Advantages of Antisense Drugs for the Treatment of Oral Diseases", Antisense and Nucleic Acid Drug Development 12, 183-191 (2002).
Nedbal, W , et al., "Antisense-Mediated Inhibition of ICAM-1 Expression: A Therapeutic Strategy Against Inflammation of Human Periodontal Tissue", Antisense & Nucleic Acid Drug Development 12, 71-78 (2002).
Patent Cooperation Treaty , International Search Report and Written Opinion for PCT/EP2020/050866, 15 pages, dated Apr. 16, 2020.
Sheshala, R , et al., "Investigation on solution-to-gel characteristic of thermosensitive and mucoadhesive biopolymers for the development of moxifloxacin-loaded sustained release periodontal in situ gels", Drug Delivery and Translational Research 9, 434-443 (2019).

* cited by examiner

*Primary Examiner* — Abigail VanHorn
*Assistant Examiner* — Stephanie L Sullivan
(74) *Attorney, Agent, or Firm* — Viksnins Harris Padys Malen LLP

(57) ABSTRACT

The present invention relates to a composition comprising an oligonucleotide, at least two copolymers with at least two of the copolymers being Poloxamer 188 and Poloxamer 407, and a medium. The present invention further relates to a method for preparing said composition.

Figure 1:

12 Claims, 7 Drawing Sheets
Specification includes a Sequence Listing.

COMPOSITION FOR ADMINISTERING AND RELEASING OLIGONUCLEOTIDES

CROSS-REFERENCE TO RELATED APPLICATION(S)

This application claims the benefit of priority of EP Application No. 19153663.0, filed Jan. 25, 2019.

DESCRIPTION

The present invention relates to a composition comprising an oligonucleotide, at least two copolymers with at least two of the copolymers being Poloxamer 188 and Poloxamer 407, and a medium. The present invention further relates to a method for preparing said composition.

For effectively treating diseases or conditions in mammals with pharmaceuticals it is not only necessary to apply a suitable pharmaceutically active compound, but also to find suitable and efficient means for administering and releasing said compounds.

One example of a disease or condition is a chronical inflammatory disease or condition of the oral cavity in a mammal, including a gum disease, a periodontal disease, a peri-implantontial disease or mukositis or other related condition. One therapeutic approach for treating a chronic inflammatory disease or condition of the buccal/oral cavity in a mammal is the "antisense-strategy" by the use of oligonucleotides. Various oligonucleotides are known in the art to reduce or completely suppress ICAM-1 (intercellular adhesion molecule-1) gene expression in humans as a specific antisense drug. ICAM-1 is a membrane-bound protein, normally involved in cell-cell adhesive interactions and up-regulated during inflammation. The reduction of the uncontrolled morbid over-expression of ICAM-1 to basal expression level is believed to be an effective and causative therapeutic target to treat chronic inflammations and diseases based on these, including gum diseases or ultimately periodontitis. Periodontitis is a wide-spread inflammatory disease or condition of the oral cavity of mammals. Periodontitis has been linked to increased inflammation markers in the body, such as indicated by raised levels of C-reactive protein and interleukin-6. In the oral cavity of people suffering from periodontitis levels of shedded ICAM-1 (sICAM-1) are significantly increased rendering the same as an attractive molecular marker to monitor the stage of inflammation/disease. Periodontitis is linked to an increased risk of several severe diseases including stroke, myocardial infarction, increased numbers/risk of abortion and atherosclerosis. With respect to elderly individuals, periodontitis is also associated with impairments in delayed memory and calculation abilities. Therefore, there exists a strong (medical) need for pharmaceutical compositions, which can be used for suitably administering and effectively releasing such agents used for the treatment of periodontitis. In fact, for the administration and release of oligonucleotides in general there is still a need for improvement. Efficient drug delivery (administration) revealed to be difficult in the oral cavity where an improved clearing rate of the sulcus fluid surrounding affected teeth counteracts against the persistence and uptake of the drug.

Furthermore, it is not only important to find efficient compositions for delivering e.g. oligonucleotides via pharmaceutical compositions but also to provide general compositions, such as e.g. compositions for personal-care products, as e.g. tooth paste, which are able to efficiently deliver e.g. oligonucleotides.

Accordingly, the technical problem underlying the present invention is to provide simple and efficient means for administering and releasing oligonucleotides e.g. for treating diseases or conditions in mammals, in particular specialized delivery system for oral drug delivery wherein increased amounts of fluids counteract against the persistence and uptake of drugs.

The solution to the above technical problem is achieved by the embodiments characterized in the claims.

In particular, in a first aspect, the present invention relates to a composition comprising an oligonucleotide, at least two copolymers with at least two of the copolymers being selected from the group consisting of Poloxamer 188 and Poloxamer 407, and a medium. In a preferred embodiment, the composition consists of the oligonucleotide, two copolymers being Poloxamer 188 and Poloxamer 407, and the medium.

The term "oligonucleotide" as used herein relates to native, semi-synthetic, synthetic or (chemically) modified, single or double stranded nucleic acid molecules of deoxyribonucleotides and/or ribonucleotides and/or modified nucleotides. Suitable modified nucleotides comprise nucleotides with modified bases, sugars, and/or phosphate groups, such as monophosphorothioate-modified internucleotide phosphates. Methods for the preparation, isolation and/or purification of oligonucleotides are known in the art and comprise chemical synthetic or enzymatic methods and subsequent purification of the oligonucleotides. In a preferred embodiment, the oligonucleotide is a single- or double-stranded oligonucleotide, preferably a single stranded modified oligonucleotide of the chemistries outlined above, more preferably an oligonucleotide with monophosphorothioate-modified internucleotide phosphates and even more preferably a gapmer oligonucleotide with monophosphorothioate-modified internucleotide phosphates.

Herein the term "gapmer oligonucleotide" refers to an oligonucleotide comprising a central single stranded DNA oligonucleotide sequence flanked on one or both ends by single stranded 2'-O-methyl RNA oligonucleotide sequences. The RNA oligonucleotide sequences each preferably have a length of 3 to 7, more preferably 4, oligonucleotides. Preferably, the gapmer oligonucleotide is a second-generation gapmer oligonucleotide, comprising 2'-O-methyl recognition arms flanking a deoxyribonucleic acid core to invoke specific RNAse H activity and successive target mRNA cleavage.

In specific embodiments, the oligonucleotide of the present invention comprises a fragment of the nucleotide sequence according to SEQ ID NO: 1 having at least 10, at least 12, at least 15, or 18 nucleotides of SEQ ID NO: 1, i.e., said fragments have 10, 12, 15, or 18 nucleotides of SEQ ID NO: 1. Preferably, said oligonucleotide consists of said fragments, i.e., said oligonucleotide has a length of 10, 12, 15, or 18 nucleotides. An oligonucleotide comprising said fragments preferably has a length of at least 10, 12, 15, or 18 nucleotides, and at most 50 nucleotides or less, more preferably 40 nucleotides or less, more preferably 35 nucleotides or less, more preferably 30 nucleotides or less, and most preferably 25 nucleotides or less.

In a particularly preferred embodiment, the oligonucleotide of the present invention comprises the entire nucleotide sequence according to SEQ ID NO: 1. Preferably, said oligonucleotide consists of said nucleotide sequence, i.e., said oligonucleotides has a length of 20 nucleotides. An oligonucleotide comprising said nucleotide sequence preferably has a length of 20 to 50 nucleotides, more preferably 20 to 40 nucleotides, more preferably 20 to 35 nucleotides, more preferably 20 to 30 nucleotides, and most preferably 20 to 25 nucleotides.

The concentration of the oligonucleotide in the composition of the present invention is not particularly limited. For example, the concentration of the oligonucleotide in the composition may be from 1.0 pM to 10 M, preferably from 0.10 µM to 5.0 M, more preferably from 1.0 µM to 500 mM, more preferably from 10 µM to 500 µM, even more preferably from 50 µM to 200 µM.

The term "copolymer" is not specifically limited and includes alternating copolymers, periodic copolymers, statistical copolymers, and block copolymers. Preferably, the copolymers according to the present invention are block copolymers, preferably non-ionic triblock copolymers.

According to the present invention, at least two copolymers are contained in the composition. The number of the different copolymers is not particularly limited. Therefore, the composition may contain two, three, four, or even more different copolymers. Preferably, the composition contains two copolymers.

The total content of the copolymers in the composition is not particularly limited. For example, the total content of the copolymers in the composition may be from 10 to 50 mass %, preferably from 15 to 45 mass %, most preferably from 20 to 40 mass %, based on 100 mass % of the composition.

According to the present invention at least two of the copolymers are Poloxamer 188 and Poloxamer 407. Preferably, the composition contains two copolymers and the copolymers are Poloxamer 188 and Poloxamer 407. Poloxamers are triblock copolymers composed of a central hydrophobic chain of poly(propylene oxide) flanked by two hydrophilic chains of poly(ethylene oxide).

The ratio of the mass of Poloxamer 188 to the mass of Poloxamer 407 in the composition is not particularly limited. For example, the ratio of the mass of Poloxamer 188 to the mass of Poloxamer 407 in the composition may be from 5:1 to 1:10, preferably from 4:1 to 1:8, more preferably from 2:1 to 1:5, more preferably from 1:1 to 1:3, due to improved physical and processing-related properties (such as viscosity and fluidity).

The medium is not particularly limited. For example, the medium may be an aqueous medium, a medium based on one or more organic solvents, or a medium based on a mixture of water with one or more organic solvents. The medium may contain salts and may have a specific pH. Preferably, the medium is selected from the group consisting of water, phosphate buffered saline (PBS), and glycine. Preferably, the medium is water, in particular aqua ad iniectabilia (cf. e.g. European Pharmacopoeia, 00169, Water for injections).

The composition may undergo sol-gel transition. Thereby, the sol-gel transition temperature of the composition is not particularly limited. For example, the sol-gel transition temperature of the composition may be from 25 to 35° C., preferably from 27 to 33° C., more preferably from 28 to 31° C. The composition is preferably in a liquid state at temperatures present in a fridge (such as from 2 to 8° C.) and is a semi-solid/gel at body temperature (such as 37° C.). In particular, when treating inflammatory regions, wherein increased amounts of fluids counteract against the persistence and uptake of drugs, such properties preferably ensure the persistence of the composition on site during treatment together with the easy handling and application of the composition, in particular in the oral cavity, preferably on the oral mucosa or the periodontal pocket, of a mammal.

In a preferred embodiment, the composition according to the present invention can be used in a method of preventing or treating a disease or condition in a mammal, preferably an inflammatory disease or condition of a superficial organ, such as e.g. the mucosa or the skin, in a mammal, more preferably an inflammatory disease or condition of the oral cavity, preferably of the oral mucosa or the periodontal pocket, in a mammal. Preferably, the inflammatory disease or condition of the oral cavity to be prevented or treated is a chronical inflammation of the gum, e.g. a periodontal disease or condition, more preferably a periodontal disease or condition selected from the group consisting of gingivitis, chronic periodontitis, aggressive periodontitis, periodontitis and peri-implantitis or mukositivis as a manifestation of systemic disease, necrotizing ulcerative gingivitis, necrotizing ulcerative periodontitis, abscesses of the periodontium, and combined periodontic-endodontic lesions.

For application to the gum or oral mucosa of a mammal, the composition preferably comprises 25 to 35 mass % of Poloxamer 407, 5 to 15 mass % of Poloxamer 188, and 55 to 65 mass % of the medium, more preferably comprises 26 to 31 mass % of Poloxamer 407, 7 to 13 mass % of Poloxamer 188, and 57 to 64 mass % of the medium, and most preferably comprises 27 to 29 mass % of Poloxamer 407, 10 to 12 mass % of Poloxamer 188, and 60 to 62 mass % of the medium based on the total mass of Poloxamer 407, Poloxamer 188, and the medium. The composition preferably contains oligonucleotides at concentrations in the range of 1.0 nM (nanomolar) to 100 µM (micromolar).

For application to the periodontal pocket of a mammal, the composition preferably comprises 15 to 25 mass % of Poloxamer 407, 5 to 15 mass % of Poloxamer 188, and 65 to 75 mass % of the medium, more preferably comprises 17 to 23 mass % of Poloxamer 407, 7 to 13 mass % of Poloxamer 188, and 67 to 73 mass % of the medium, and most preferably comprises 19 to 21 mass % of Poloxamer 407, 9 to 11 mass % of Poloxamer 188, and 69 to 71 mass % of the medium based on the total mass of Poloxamer 407, Poloxamer 188, and the medium. The composition preferably contains oligonucleotides at concentrations in the range of 1.0 nM (nanomolar) to 100 µM (micromolar).

The nature of the composition according to the present invention is not particularly limited. For example, the composition may be a pharmaceutical composition or a composition for personal-care products, such as e.g. tooth paste, or a composition for cosmetic applications. Preferably, the composition according to the present invention is a pharmaceutical composition.

In a preferred embodiment, the composition comprises the oligonucleotide in a pharmaceutically active amount. The composition may further optionally contain a acceptable carrier, excipient or diluent. In order to enhance bioadhesive properties, bioadhesive polyacrylic acid-based excipients (e.g. Carbopol) or cellulose-based (e.g. carboxymethylcellulose), but also (partially) natural substances such as alginates, chitosan, etc., may also be included in the composition. Polyvinyl alcohols may also be included in the composition as bioadhesive agents.

The pharmaceutical composition may be administered by any administration route known in the art being suitable for delivering a medicament to a mammal. The route of administration does not exhibit particular limitations and includes for example oral application, (topical) dermal application, local application, other forms of topic application (e.g. in the use of delivery devices).

The composition of the present invention is preferably able to release an oligonucleotide in tissue, especially including mucosa tissue, more efficiently as compared to a control not containing the copolymers according to the present invention. Moreover, the released oligonucleotide is preferably not degraded by the formulation process. Furthermore, the composition of the present invention preferably allows controlled spacial and temporal release, the substantial lowering of the whole body exposure to the corresponding drug, i.e. lowering costs and avoiding side effects (off-target effects), and the adaptation of the composition to specific clinical or technical requirements.

In a further aspect, the present invention relates to a method of preventing or treating a disease or condition in a mammal comprising administering the composition according to the present invention to a mammal. The above statements and definitions analogously apply to this aspect of the present invention. In particular, the above-mentioned preferred prevented or treated diseases or conditions analogously apply to this aspect of the present invention.

In a further aspect, the present invention relates to a cosmetic method comprising applying the composition according to the present invention to a mammal, preferably a human. The above statements and definitions analogously apply to this aspect of the present invention. The route of administration/application does not exhibit particular limitations and includes for example oral application, (topical) dermal application, local application, other forms of topic application (e.g. in the use of delivery devices), preferably (topical) dermal application.

In a further aspect, the present invention relates to a method for preparing the composition according to the present invention, comprising the steps of
(a) mixing the oligonucleotide, the copolymers, and the medium and
(b) stirring the mixture.

The above definitions analogously apply to this aspect of the present invention.

The method for preparing the composition is not further specifically limited. Thus, for example any method fulfilling the above conditions can be used for preparing the composition according to the present invention. For example, the composition may be prepared by the cold method.

The temperature in the step (a) is not particularly limited. For example, the temperature of the medium in the step (a) may be adjusted to 0° C. to 10° C. before, between, and/or after mixing the medium with the other components of the composition. Preferably, the temperature of the medium in the step (a) is adjusted to 2 to 8° C., more preferably to 3 to 5° C. before, between, and/or after mixing the medium with the other components of the composition.

The order in which the components of the composition are mixed in step (a) is not particularly limited. For example, the oligonucleotide might first be dissolved in the medium before the remaining components are added.

The temperature in the step (b) is not particularly limited. For example, the step (b) may comprise stirring the mixture at a temperature of from 0° C. to 10° C. Preferably, the temperature of the medium in the step (b) is from 2 to 8° C., more preferably from 3 to 5° C.

The duration of the stirring in the step (b) is not particularly limited. For example, the step (b) may comprise stirring the mixture for 1 min to 96 h. Preferably, the duration of the stirring in the step (b) is from 1 h to 72 h, more preferably from 12 h to 60 h, more preferably from 36 h to 54 h.

Figure 2:
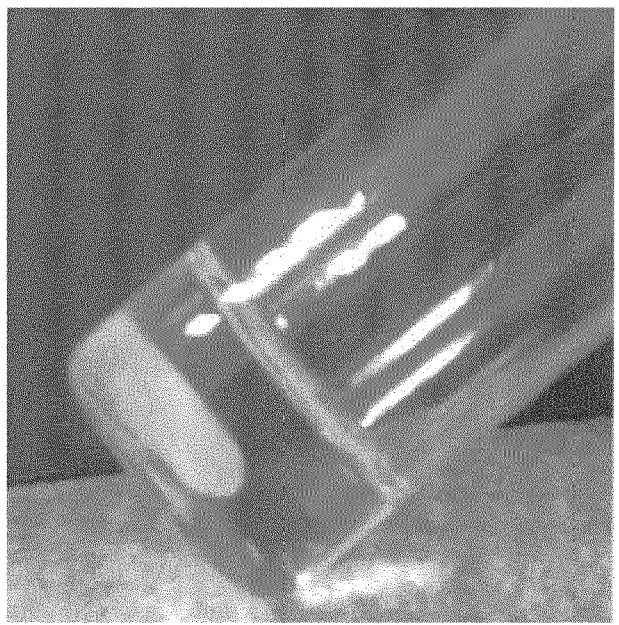
Figure 2:
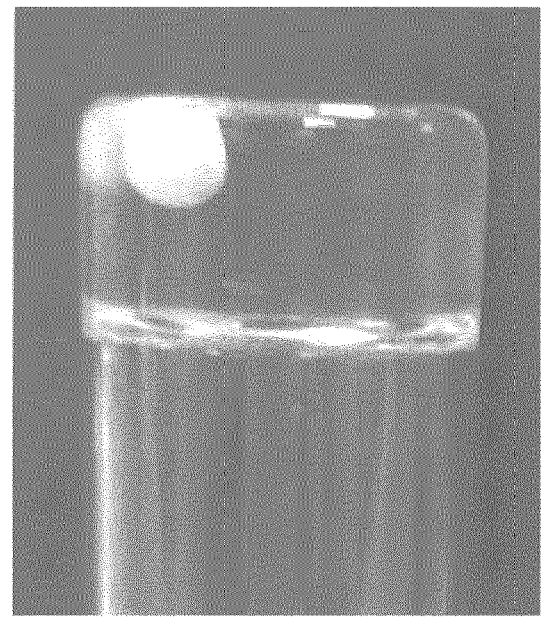
Figure 3:
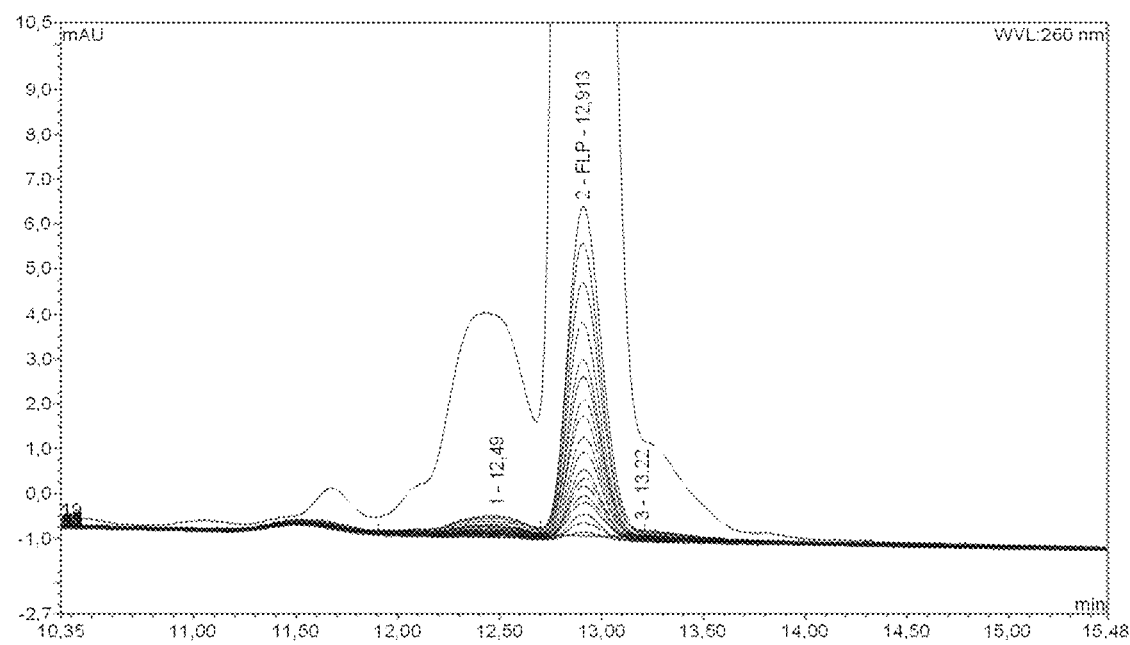
Figure 4:
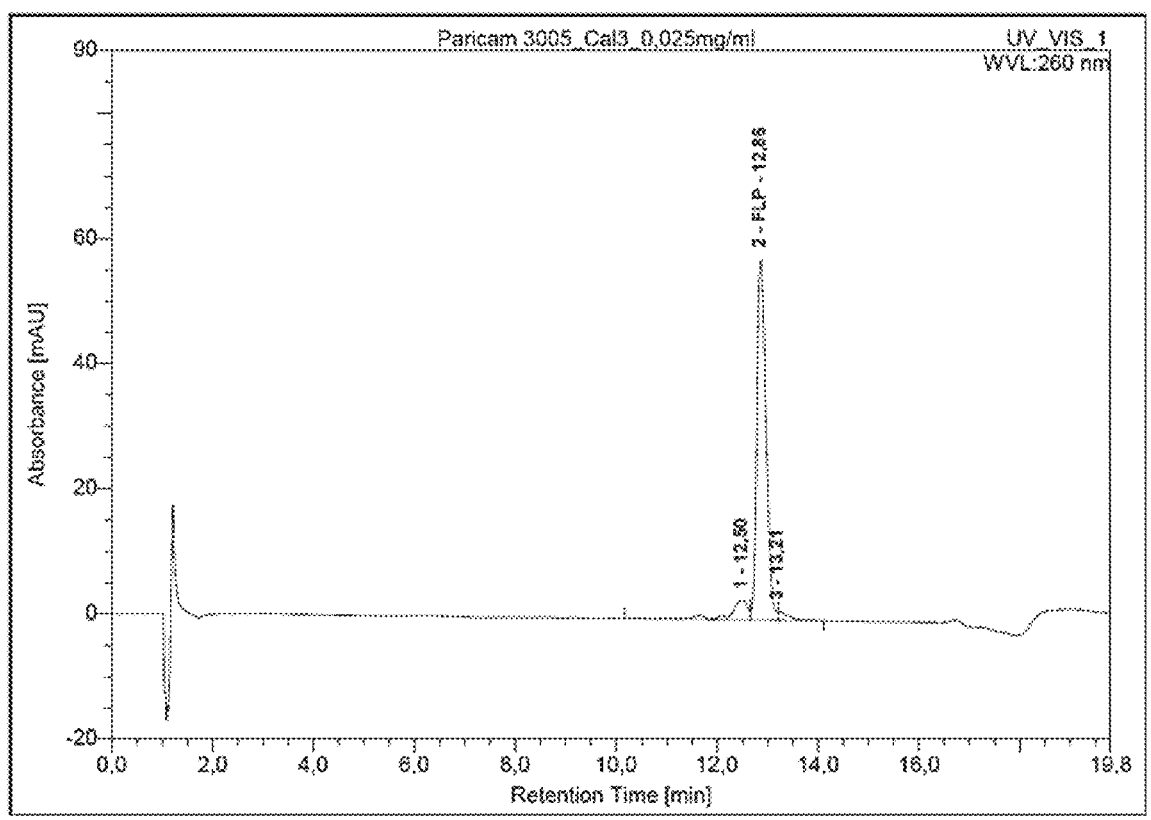
Figure 5:
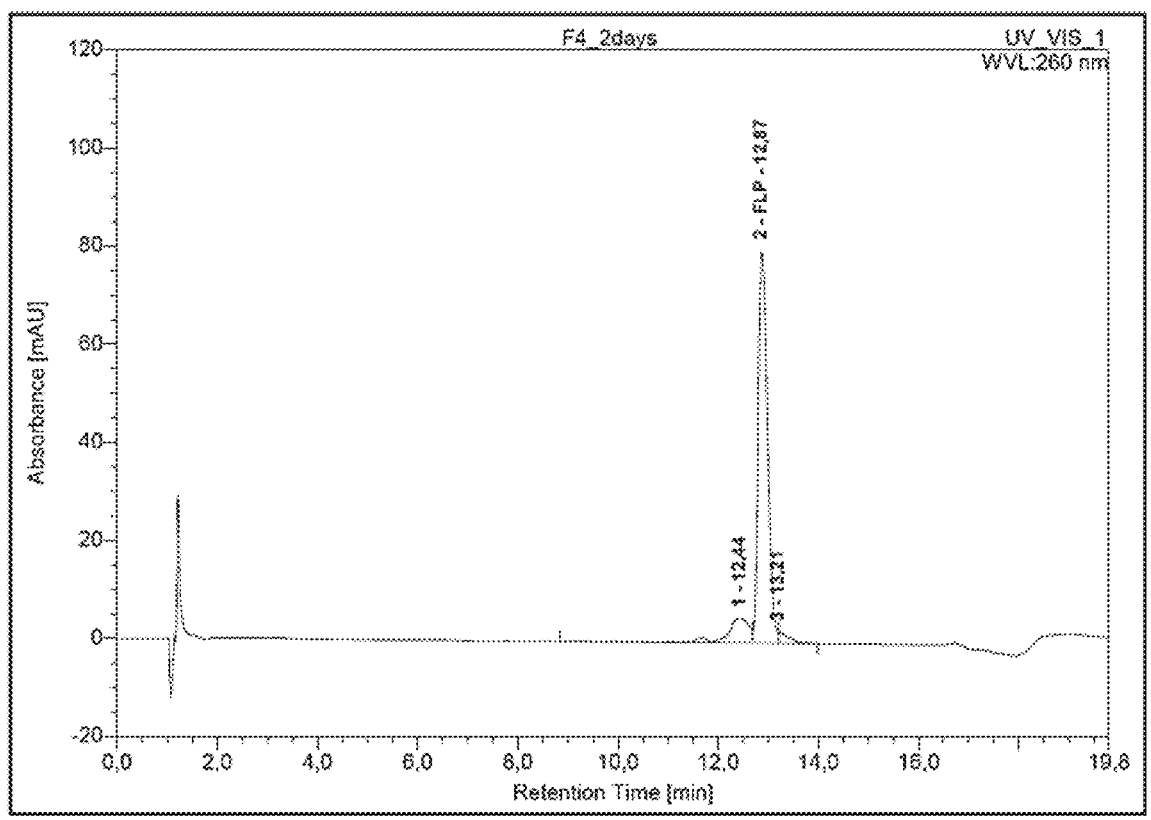
Figure 6:
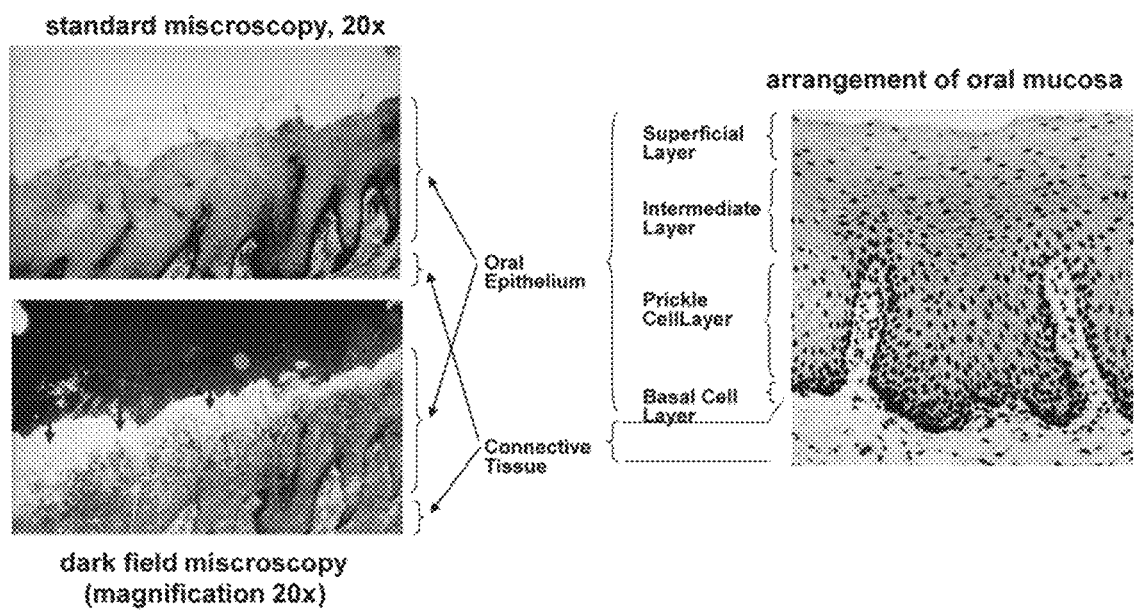
Figure 7:
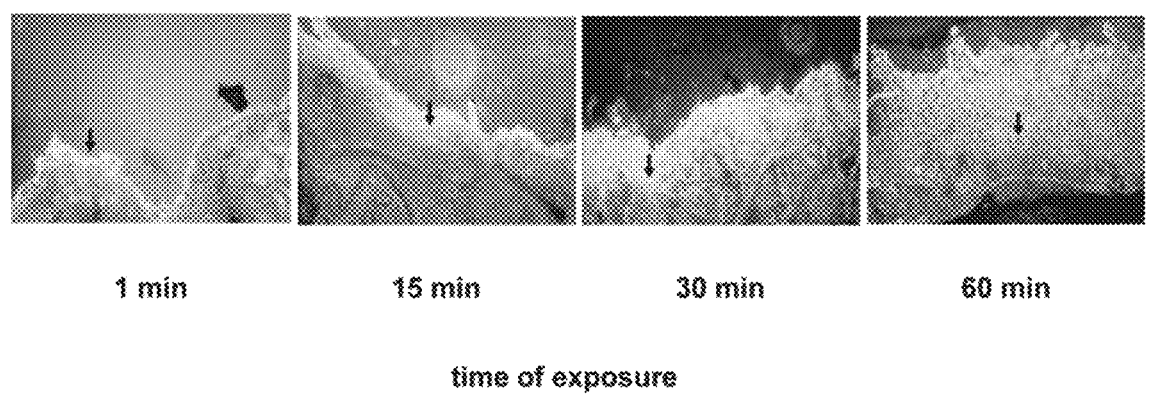
Figure 8:
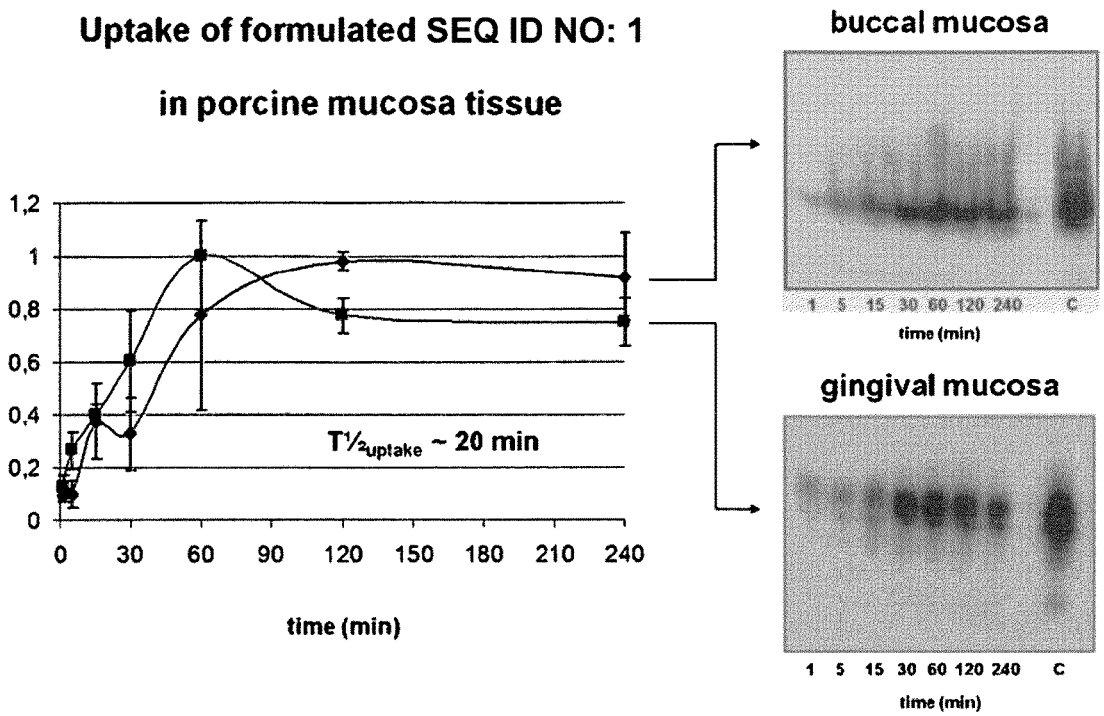
Figure 9:
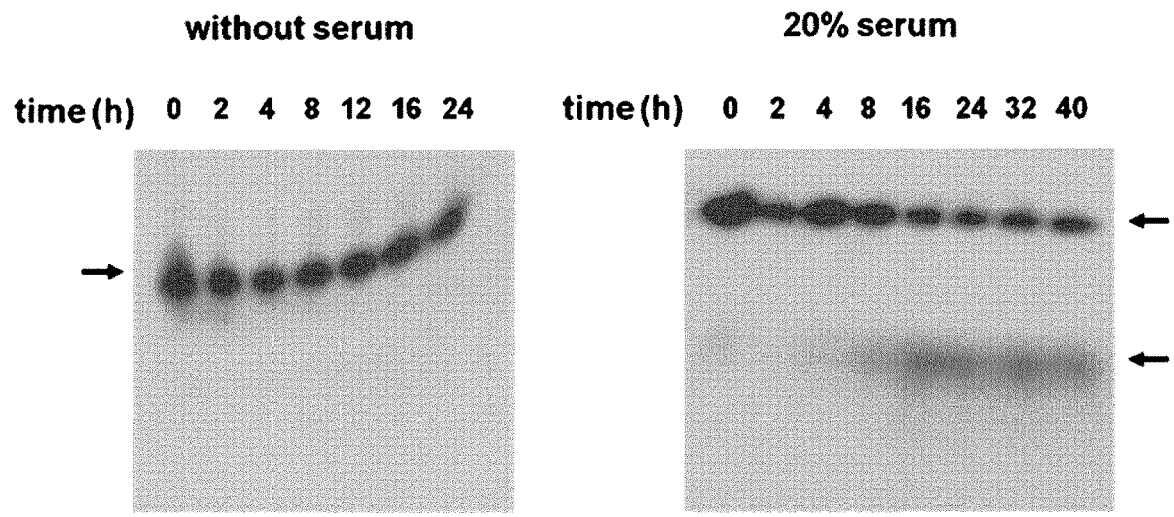

The figures show:
FIG. 1: The state of formulation 4 at 18° C. before sol-gel transition.
FIG. 2: The state of formulation 4 at 37° C. after sol-gel transition.
FIG. 3: AEX-HPLC traces of the nucleotide sequence according to SEQ ID NO: 1 released from the formulation F4 over time during dialysis.
FIG. 4: HPLC traces for the unformulated nucleotide sequence according to SEQ ID NO: 1 (FIG. 4).
FIG. 5: HPLC traces for the nucleotide sequence according to SEQ ID NO: 1 released from a composition according to the present invention (FIG. 5).
FIG. 6: Uptake and distribution of antisense oligonucleotide of SEQ ID NO: 1 in porcine oral mucosa tissue by the use of the composition according to the present invention. 5-prime radioactively labelled oligonucleotide ($\alpha^{32}$P-UTP-labelled phosphorothioate-modified PS-ON) was formulated in the composition according to the present invention and applied to the mucosa for different time points. Cryostat sections of the tissue were performed (left side) and oligonucleotides visualized by contact emulsion autoradiography. Arrangement of porcine oral mucosa (left side) and human mucosa (right side) is similar. Oligonucleotides can be seen as white spots in all layers of the oral epithelium in dark field microscopy (left side).
FIG. 7: Kinetics of formulated oligonucleotide of SEQ ID NO: 1 delivery in porcine mucosa tissue ex vivo 5-prime radioactively labelled oligonucleotide of SEQ ID NO: 1 ($\alpha^{32}$P-UTP-labelled phosphorothioate-modified PS-ON) was formulated in the composition according to the present invention and applied to the mucosa for different time points as indicated. Cryostat sections of the tissue were performed and oligonucleotides visualized by contact emulsion autoradiography (white spots). A homogeneous distribution of the formulated oligonucleotide could be observed after 60 minutes of incubation.
FIG. 8: Quantification of uptake kinetics of formulated oligonucleotide of SEQ ID NO: 1 in porcine buccal and gingival mucosa tissue. 5-prime radioactively labelled oligonucleotide of SEQ ID NO: 1 ($\alpha^{32}$P-UTP-labelled phosphorothioate-modified PS-ON) was formulated in the composition according to the present invention and applied to porcine mucosa tissue ex vivo (buccal: blue line; gingival: red line) for different time points. Samples (at triplicates) were withdrawn at indicated time points and oligonucleotides of SEQ ID NO: 1 were extracted from the tissue and analyzed by PAGE. Quantification was performed using a Phosphorimager (Perkin Elmer®). Quantification revealed half times of drug delivery between approx. 20 minutes (gingival mucosa) and 45 minutes (buccal mucosa). C=full length oligonucleotide not applied to tissue for internal control (size/stability).
FIG. 9: Stability of the oligonucleotide according to SEQ ID NO: 1 in the absence (left) or presence (right) of human serum in vitro.

The present invention will be further illustrated in the following examples without being limited thereto.

Materials:
Poloxamer 188 (CAS No. 9003-11-6) and Poloxamer 407 (CAS No. 9003-11-6) were purchased from Sigma Aldrich. PBS was purchased from Biochrom GmbH. All of these materials had a grade for biology use.

EXAMPLE 1: FORMULATION 0 (F0)

To 1 mL of water at 4° C. were added 100 mg Poloxamer 188. The mixture was stirred at 4° C. until the polymer was dissolved, then 250 mg Poloxamer 407 were added to the mixture. After 8 h stirring at 4° C. a clear solution was obtained.

EXAMPLE 2: FORMULATION 1 (F1)

To 7 g of water at 4° C. were added 1 g Poloxamer 188 and 2 g Poloxamer 407. The mixture was stirred for 48 h at 4° C. until the polymers were dissolved and a clear solution was obtained.

EXAMPLE 3: FORMULATION 2 (F2)

To 7.03 g of 1×PBS at 4° C. were added 1 g Poloxamer 188 and 2 g Poloxamer 407. The mixture was stirred for 48 h at 4° C. until the polymers were dissolved and a clear solution was obtained.

EXAMPLE 4: FORMULATION 3 (F3)

To 3.50 g of 1×PBS were added 0.30 mg of the nucleotide sequence according to SEQ ID NO: 1 (21 µL; 15 mg/mL). The solution was cooled to 4° C. and then 0.50 g Poloxamer 188 and 1.00 g Poloxamer 407 were added. The mixture was stirred for 48 h at 4° C. until the polymers were dissolved and a clear solution was obtained.

EXAMPLE 5: FORMULATION 4 (F4)

To 3.29 g of 1×PBS were added 3.15 mg of the nucleotide sequence according to SEQ ID NO: 1 (210 µL; 15 mg/mL). The solution was cooled to 4° C. and then 0.50 g Poloxamer 188 and 1.00 g Poloxamer 407 were added. The mixture was stirred for 48 h at 4° C. until the polymers were dissolved and a clear solution was obtained.

EXAMPLE 6: DETERMINATION OF THE SOL-GEL TEMPERATURES OF FORMULATIONS F1 TO F4

Sol-gel temperatures were determined for the different formulations. The sol-gel transition point was measured by the magnetic stirrer method. Thereby, the respective formulation is heated to 40° C. in 30 min with constant magnetic stirring (100 rpm) and the temperature at which the stirrer stops rotating is considered as sol-gel transition temperature. The results are summarized in Table 1. The state of formulation 4 before and after sol-gel transition is depicted in FIGS. 1 and 2, respectively.

TABLE 1

| Formulation | Temperature (° C.) | Temperature (° C.) |
| --- | --- | --- |
| F1 | 33.0 | 33.6 |
| F2 | 31.0 | 30.7 |
| F3 | 30.6 | 30.0 |
| F4 | 29.0 | 29.1 |

EXAMPLE 7: DETERMINATION OF THE RNA RELEASE BY DIALYSIS FOR THE FORMULATION F4 AND A FORMULATION CONTAINING THE RNA IN PBS

A vial containing 25 mL of PBS was warmed up to 37° C., and kept at this temperature. A dialysis tube (MWCO 300 kD, Float-A-Lyzer G2, Spectrum Labs) pre-wetted at 37° C., was placed in the PBS vial and 1 mL of formulation F4 (4° C.) was filled in the tube via a syringe. The formulation was dialyzed for 90 min and for each time point 50 µL of the buffer solution was collected. The RNA concentration was determined by AEX HPLC (Dionex Ultimate 3000 UPLC using a DNA Pac PA 200 column) for each sample. The RNA concentration in F4 is 30 µg/mL. The results are summarized in Table 2. AEX-HPLC traces of the nucleotide sequence according to SEQ ID NO: 1 released from the formulation F4 over time are depicted in FIG. 3.

TABLE 2

| Time point (min) | Oligonucleotide conc. (µg/mL) | % |
| --- | --- | --- |
| 5 | 0.15 | 0.6 |
| 10 | 0.32 | 1.3 |
| 15 | 0.48 | 1.9 |
| 20 | 0.63 | 2.5 |
| 30 | 0.93 | 3.6 |
| 40 | 1.28 | 5.0 |
| 50 | 1.65 | 6.4 |
| 60 | 1.97 | 7.7 |
| 70 | 2.35 | 9.2 |
| 80 | 2.68 | 10.5 |
| 90 | 3.04 | 11.9 |
| 48 h | 35.25 | 100.0 |

The same procedure was applied to a solution of the nucleotide sequence according to SEQ ID NO: 1 (1 mg/mL) in PBS as a control. The solution was dialyzed for 240 min at 37° C. and for each time point 50 µL of the buffer solution were collected. The RNA concentration was determined for each sample by UV measurements (Eppendorf BioPhotometer D30). The results are summarized in Table 3.

TABLE 3

| Time point (min) | Oligonucleotide conc. (µg/mL) | % |
| --- | --- | --- |
| 5 | 1.2 | 3.0 |
| 10 | 1.9 | 4.7 |
| 30 | 1.6 | 4.0 |
| 60 | 1.7 | 4.3 |
| 90 | 2.4 | 6.0 |
| 120 | 3.1 | 7.8 |
| 180 | 3.9 | 9.8 |
| 240 | 5.1 | 12.8 |
| 48 h | 27.6 | 69.0 |

EXAMPLE 8: COMPARISON OF THE HPLC TRACES OF UNFORMULATED AND FORMULATED NUCLEOTIDE SEQUENCE ACCORDING TO SEQ ID NO: 1

HPLC traces were recorded for unformulated (i.e. neat) (FIG. 4) and formulated (FIG. 5) nucleotide sequence according to SEQ ID NO: 1. FIGS. 4 and 5 clearly demonstrate that the formulation process does not result in a degradation of the oligonucleotide.

EXAMPLE 9: UPTAKE OF THE NUCLEOTIDE SEQUENCE ACCORDING TO SEQ ID NO: 1 IN HUMAN ORAL MUCOSA TISSUE USING THE COMPOSITION ACCORDING TO THE PRESENT INVENTION

To investigate uptake and distribution of the nucleotide sequence according to SEQ ID NO: 1 included in the composition according to the present invention in the mucosa, 5-prime radioactively labelled oligonucleotide according to SEQ ID NO: 1 ($\alpha^{32}$P-UTP-labelled phosphorothioate-modified PS-ON) was formulated in the composition according to the present invention and applied to porcine mucosa tissue which is very similar to the human gingival ex vivo. After incubation cryostat sections were performed (FIG. 6, left side) and the oligonucleotides visualized by contact emulsion autoradiography. Arrangement of porcine oral mucosa (FIG. 6, left side) and human mucosa (FIG. 6, right side) is similar. Oligonucleotides can be seen as white spots in all layers of the oral epithelium in dark field microscopy (FIG. 6, left side).

Accumulation of more than 60% of the applied oligonucleotides in the keratinized layer was observed within several minutes (not shown), and the intermediate layer, prickle cell layer and basal cell layer also were reached in a time-dependent manner (FIG. 6). After one to two hours again accumulation of oligonucleotides at the basement membrane occurs indicating an additional protective function of this membrane within the healthy skin (not shown). However, in case of inflammation the basement membrane becomes more flexible and permeable due to the destruction by enzymatic degradation of invasive leukocytes.

EXAMPLE 10: KINETICS OF THE DELIVERY OF THE NUCLEOTIDE SEQUENCE ACCORDING TO SEQ ID NO: 1 IN ORAL MUCOSA TISSUE EX VIVO

The time course of an uptake of the nucleotide sequence according to SEQ ID NO: 1 included in the composition according to the present invention on oral mucosa tissue (porcine buccal and gingival mucosa tissue) was studied (FIGS. 7 and 8; in FIG. 8: buccal: blue line; gingival: red line). Experiments were performed as described in Example 9 and kinetics were performed by taking samples at indicated time points. Cryostat sections of the tissue were performed and oligonucleotides visualized by contact emulsion autoradiography (FIG. 7, white spots). A homogeneous distribution of the formulated oligonucleotide could be observed after 60 minutes of incubation. Samples (at triplicates) were withdrawn at indicated time points and oligonucleotides were extracted from the tissue and analyzed by PAGE (FIG. 8). Quantification was performed using a Phosphorimager (Perkin Elmer®). The quantification of the uptake kinetics revealed half times of drug delivery between approximately 20 minutes (gingival mucosa) and 45 minutes (buccal mucosa).

EXAMPLE 11: STABILITY OF THE NUCLEOTIDE SEQUENCE ACCORDING TO SEQ ID NO: 1 UNDER EXPERIMENTAL CONDITIONS

To test stability of the nucleotide sequence according to SEQ ID NO: 1, the oligonucleotide was 5'-radiolabeled and incubated either in the absence or in the presence of human serum (20%) for different time points. Samples were analyzed by PAGE and checked for degradation products. As seen in FIG. 9 no degradation products could be observed in the absence of serum at all, whereas slight degradation was visible in the presence of serum (20%) after 8 to 16 hours (upper arrow: full length oligonucleotide, lower arrow: degradation products).

The present invention relates to the following nucleotide sequence.

SEQ ID NO: 1
5'-mA-mU-m(5mC)-mA-G-A-T-G-(5mC)-G-T-G-G-(5mC)-(5mC)-T-mA-mG-mU-mG-3'

N=2'-deoxy nucleoside;
mN=2'-O-methyl nucleoside;
5 mC=2'-deoxy-5-methyl-cytidine;
m(5 mC)=2'-O-methyl 5-methyl-cytidine;
all internucleotide phosphates are monophosphorothioate-modified.

The invention claimed is:

1. A composition comprising an oligonucleotide, at least two copolymers with at least two of the copolymers being Poloxamer 188 and Poloxamer 407, and a medium, wherein the oligonucleotide comprises the nucleotide sequence according to SEQ ID NO:1.

2. The composition according to claim 1, wherein the ratio of the mass of Poloxamer 188 to the mass of Poloxamer 407 in the composition is from 5:1 to 1:10.

3. The composition according to claim 1, wherein the medium is one or more selected from the group consisting of water, PBS, and glycine.

4. The composition according to claim 1, wherein a sol-gel transition temperature of the composition is from 25 to 35° C.

5. The composition according to claim 1, wherein the concentration of the oligonucleotide is from 1.0 pM to 10 M.

6. The composition according to claim 1, wherein the composition is a pharmaceutical composition.

7. A method of treating an inflammatory disease or condition of the oral cavity in a mammal, comprising administering to the oral cavity of the mammal an amount of the composition of claim 1 to treat the inflammatory disease or condition of the oral cavity, wherein the inflammatory disease or condition of the oral cavity is a periodontal disease or condition.

8. The method of claim 7, wherein the periodontal disease or condition is selected from the group consisting of gingivitis, chronic periodontitis, aggressive periodontitis, peri-odontitis and peri-implantitis or mukositivis as a manifestation of systemic disease, necrotizing ulcerative gingivitis, necrotizing ulcerative periodontitis, abscesses of the periodontium, and combined periodontic-endodontic lesions.

9. The method of claim 7, wherein the administration of the composition to the oral cavity is via dermal application.

10. A method for preparing the composition according to claim 1, comprising the steps of
    (a) mixing the oligonucleotide, the copolymers, and the medium and
    (b) stirring the mixture.

11. The method according to claim 10, wherein the temperature of the medium in the step (a) is adjusted to 0° C. to 10° C. before, between, and/or after mixing the medium with the other components of the composition.

12. The method according to claim 10, wherein the step (b) comprises stirring the mixture for 1 min to 96 h at a temperature of from 0° C. to 10° C.

\* \* \* \* \*

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Gapmer oliguncleotide with a central single
      stranded DNA oligonucleotide sequence flanked on both ends by
      single stranded 2'-O-methyl RNA oligonucleotide sequences and
      having phosphorothioate-modified internucleotide phosphates
<220> FEATURE:
<221> NAME/KEY: misc_feature
<222> LOCATION: (1)..(4)
<223> OTHER INFORMATION: 2'-O-methyladenosine, um, 2'-O-methyl-5-
      methylcytidine, 2'-O-methyladenosine
<220> FEATURE:
<221> NAME/KEY: misc_feature
<222> LOCATION: (1)..(20)
<223> OTHER INFORMATION: phosphorothioate-modified internucleotide
      phosphates
<220> FEATURE:
<221> NAME/KEY: misc_feature
<222> LOCATION: (9)..(9)
<223> OTHER INFORMATION: 2'-deoxy-5-methylcytidine
<220> FEATURE:
<221> NAME/KEY: misc_feature
```

```
<222> LOCATION: (14)..(15)
<223> OTHER INFORMATION: 2'-deoxy-5-methylcytidine, 2'-deoxy-5-
      methylcytidine
<220> FEATURE:
<221> NAME/KEY: misc_feature
<222> LOCATION: (17)..(20)
<223> OTHER INFORMATION: 2'-O-methyladenosine, gm, um, gm

<400> SEQUENCE: 1
ancagatgcg tggcctannn                                               20
```